United States Patent [19]

Ripka

[11] 4,077,954

[45] Mar. 7, 1978

[54] N-(p-METHYLPHENETHYL)-4-ARYL-TRANS-DECAHYDROISOQUINOLINES

[75] Inventor: William Charles Ripka, Wilmington, Del.

[73] Assignee: E. I. Du Pont de Nemours and Company, Wilmington, Del.

[21] Appl. No.: 749,985

[22] Filed: Dec. 13, 1976

Related U.S. Application Data

[63] Continuation-in-part of Ser. No. 656,894, Feb. 10, 1976, abandoned.

[51] Int. Cl.$^2$ ............................................ C07D 217/16

[52] U.S. Cl. ........................ 260/289 D; 260/283 SY; 424/258

[58] Field of Search ..................................... 260/289 D

[56] References Cited

FOREIGN PATENT DOCUMENTS 802,557  11/1973  Belgium ............................. 260/289

*Primary Examiner*—Donald G. Daus
*Assistant Examiner*—David B. Springer
*Attorney, Agent, or Firm*—Anthony P. Mentis

[57] ABSTRACT

N-(p-methylphenethyl)-4a-aryl-trans-decahydroisoquinolines useful as analgesics.

5 Claims, No Drawings

N-(p-METHYLPHENETHYL)-4a-ARYL-TRANS-DECAHYDROISOQUINOLINES

CROSS-REFERENCE TO RELATED APPLICATIONS

This application is a continuation-in-part of applicant's copending application Ser. No. 656,894, filed Feb. 10, 1976, now abandoned.

BACKGROUND

This invention relates to decahydroisoquinoline analgesics.

Boekelheide and Schilling, J. Am. Chem. Soc. 72, 712 (1950), disclosed the compound N-methyl-4a-phenyl-decahydroisoquinoline (naming it "N-methyl-10-phenyldecahydroisoquinoline) and indicated that only one of the possible forms, presumably the cis, was present; also that it had low analgesic activity.

Finch, et. al., J. Org. Chem. 39, 8, 1118 (1974) disclosed that the compound prepared by the Boekelheide process has the trans stereochemistry.

Eddy, J. Am. Pharm. Assoc. 34, 245 (1950), in relating chemical structure to analgesic action, said that "one can see in the morphine framework a number of simpler structures [one of them decahydroisoquinoline] and it is easy to imagine that the whole molecule is built around any one of them. Each of the moieties by itself is relatively inert and completely devoid of analgesic action. Nevertheless, with everyone of them as a starting point, new compounds have been synthesized which exhibit some degree of "analgesic effect".

Brittelli and Ripka, Belgian Pat. No. 802,557, disclose N-phenethyl-4a-aryl-trans-decahydroisoquinolines, useful as analgesics.

The incorporation of an N-phenethyl substituent normally does not lead to lower addiction liability. An example of this is phenazocine (2'-hydroxy-5,9-dimethyl-2-phenethyl-6,7-benzomorphan, trade name Prinadol ®.) In discussing this compound Jaffe states that "although developed by May and Eddy at the National Institutes of Health, with the hope that it would be free of morphine's abuse liability, phenazocine did not fulfill this goal. The drug is a potent analgesic, but it also produces the entire range of morphine-like actions, including respiratory depression, constipation, and physical dependence." (Goodman & Gilman, the Pharmacological Basis of Therapeutics, MacMillan, 1965, p. 273).

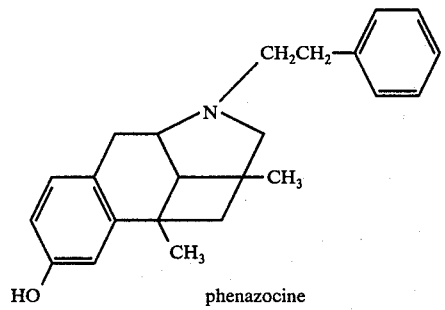

phenazocine

Phenzaocine hydrobromide has an analgesic $ED_{50}$ in mice of 0.2 mg/kg and a Straub tail $ED_{50}$ of 0.5 mg/kg (Shemano and Wendel, Toxicology and Appl. Pharmacol. 6, 334 (1964)). Therefore, the ratio of Straub tail $ED_{50}$ to analgesic $ED_{50}$ is about 2.5. In morphine this ratio ($ED_{50}^{ST}/ED_{50}^{analgesia}$) is 6.3/5.6 ≃ 1. Thus, compounds that are very addictive have a low ratio.

N-phenethyl-4a-(m-hydroxyphenyl)-trans-decahydroisoquinoline (Belgian Patent 802,557) has an oral $ED_{50}^{ST}/ED_{50}^{analgesia}$ of 10/6.6 ≃ 1.

I have found that substitution of a particular phenethyl, namely p-methylphenethyl, on the nitrogen of the 4a-aryldecahydroisoquinolines leads to compounds that are more potent as analgesics and surprisingly less potentially addicting as indicated by Straub tail. N-(p-methylphenethyl)-4a-m-hydroxyphenyl-trans-decahydroisoquinoline has an $ED_{50}^{ST}/ED_{50}^{analgesia}$ of 93/2 = 46.

SUMMARY

According to this invention, there is provided novel compounds of formula I and their pharmaceutically suitable salts, pharmaceutical compositions containing them, and methods of using them to produce analgesia in mammals.

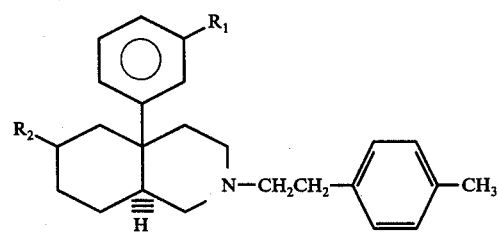

where
$R_1 =$ OH or $OCH_3$; and

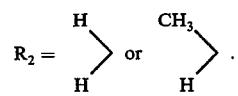

DETAILED DESCRIPTION

Stereochemistry

The compounds of formula I include various stereochemical isomers stemming from substitution at position 6 and from optical asymmetry of the whole structure. At position 6, when $R_2$ is

spatial considerations require the existence of axial and equatorial isomers. In the molecule as a whole, spatial considerations require the existence of d and l optical isomers. Optical isomers are normally present as racemic mixtures, which can be resolved by known methods (Eliel, Stereochemistry of Carbon Compounds, McGraw-Hill, 1962, p. 31).

Pharmaceutical Salts

Pharmaceutically suitable acid addition salts of these compounds include those made with physiologically acceptable acids that are known in the art; such salts include hydrochloride, sulfate, phosphate, nitrate, citrate, maleate, and the like.

Synthesis

A general synthetic procedure for preparing 4a-aryl-transdecahydroisoquinolines is disclosed in Belgian Pat. No. 802,557, Austrian Pat. No. 330,179, Hungarian Pat. No. 167,738, Luxembourg Pat. No. 68,066, Spanish Pat. No. 417,127, South African Pat. No. 73/4895, and co-pending U.S. application Ser. No. 566,089 filed Apr. 8, 1975.

The process for preparing intermediates starts with 2-cyano-3-aryl-3-carbalkoxymethylcyclohexenes that can be obtained according to procedures disclosed by Boekelheide and Schilling (loc. cit.) with respect to 2-cyano-3-phenyl-3-carbethoxy-methylcylohexene. A key step in the process is the reaction of a 2-cyano-3-aryl-3-carbalkoxymethylcyclohexene with hydrogen chloride in a lower alkanol such as ethanol to form a 4a-aryl-1,3-diketo-1,2,3,4,4a,5,6,7-octahydroisoquinoline. The 1,3-diketo-1,2,3,4,4a,5,6,7-octahydroisoquinolines possess a conformational arrangement of the fused rings which requires formation of trans-decahydroisoquinoline structures when the 8,8a-double bond is converted to a single bond.

The selection of specific preparational steps following the initial formation of a 1,3-diketo-1,2,3,4,4a,5,6,7-octahydroisoquinoline depends upon the specific derivative that is desired. The sequence involves at least three steps, illustrated as follows:

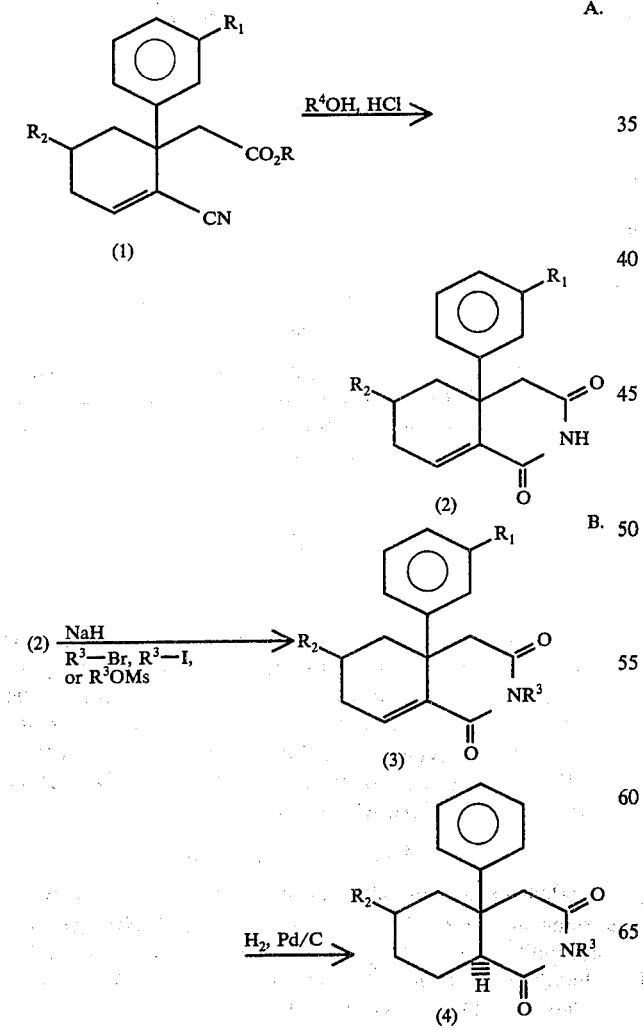

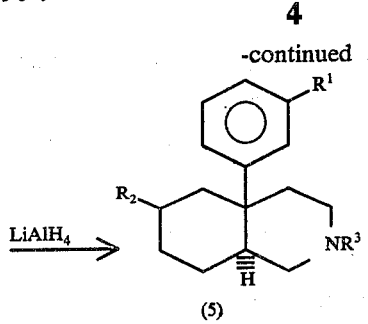

where $R^1$ and $R^2$ = as previously defined;

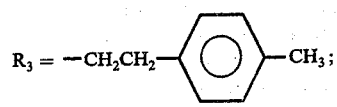

and $R^4 = C_1$–$C_4$ alkyl.

In Step A reactant $R^4OH$, which is also the reaction medium, is generally used in excess but to insure maximum yield should be used in the amount of at least one mole per mole of cyanoester. Likewise the HCl reactant may be used in excess but to insure maximum yield should be present in the amount of at least one mole per mole of cyanoester. The reaction is run in the liquid phase under anhydrous conditions. The reaction temperature should be in the range of about 50 to about 120° C. The reaction pressure is not critical, ordinarily being atmospheric for convenience but should be consistent with achievement of the stated reaction temperature.

In the preparation of a 2-cyano-3-phenyl-3-carbalkoxy-methylcyclohexene, the Boekelheide and Schilling procedure involves basically starting with cyclohexanone, as follows:

a. Cyclohexanone → 2-chlorocylohexanone (Horning, Organic Syntheses, Coll. Vol. III, 1955 p. 188)
b. 2-Chlorocyclohexanone → 2-phenylcyclohexanone (Newman et al. J. Am. Chem. Soc. 66, 1551 1944). An alternative method is shown by T. Kametani et al., J. Chem. Soc. (C), 1047 (1971) in which a chloro-substituted benzene is reacted with cyclohexanone in the presence of sodium amide to produce a 2-arylcyclohexanone.)
c. 2-Phenylcyclohexanone → 2-phenyl-2-carbethoxycyclohexanone (Newman et al., J. Am. Chem. 69, 942 (1947)).
d. 2-Phenyl-2-carbethoxycyclohexanone → 2-cyano-3-phenyl-3-carbethoxycyclohexene.

These preliminary steps lead to the different derivatives defined by the various values in formula I through starting with appropriately substituted cyclohexanones in step A and with the appropriately substituted arylmagnesium bromide (or substituted chlorobenzene in the alternative method) as intermediates in step B. Thus, 4-methylcyclohexanone which is commercially available, can be used as the basic starting material to produce compounds of formula I in which

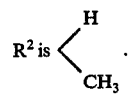

Compounds where $R^1$ is methoxy serve as intermediates for compounds where $R^1$ is hydroxy; the methoxy, or "masked hydroxy" is converted to the hydroxy by any known suitable demethylation technique.

The following examples illustrate specifically how to make the compounds of this invention. Parts are by weight and temperatures are in degrees centigrade unless otherwise stated.

EXAMPLE 1

N-(p-methylphenethyl)-4a-(m-methoxyphenyl)-trans-decahydroisoquinoline

A.

N-(p-methylphenethyl)-4a-(m-methoxyphenyl)-1,3-diketo1,2,3,4,4a,5,6,7-octahydroisoquinoline

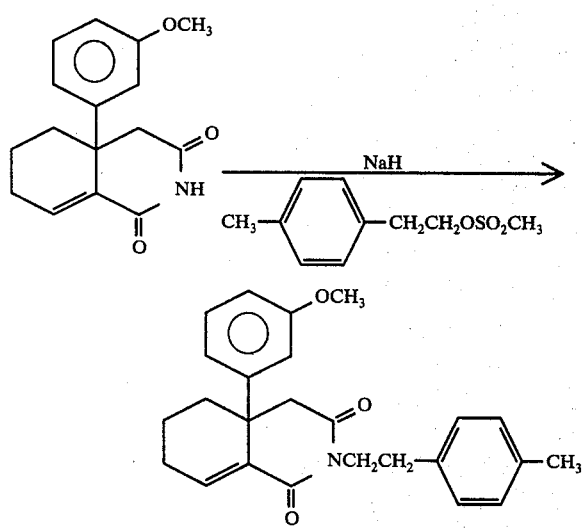

4a-(m-Methoxyphenyl)-1,3-diketo-1,2,3,4,4a,5,6,7-octahydroisoquinoline (6 g) in 75 ml of anhydrous dimethylformamide was added to a 55% suspension of sodium hydride in mineral oil (1.2 g) in 50 ml of dimethylformamide at 70°. The reaction mixture was heated for one hour at 80° and then cooled to 25°. p-Methylphenethyl mesylate (7.0 g) was added and the reaction heated at 70° for 18 hours. It was poured into water and extracted with ether. The residue after evaporation of the ether was chromatographed on 800 g. of Florisil. This yielded 4.4 g, mp 134°-140°; recrystallized from ethanol, mp 149°-151°.

HRMS: Calcd. for $C_{25}H_{27}NO_3$: 389.1196; measured: 389.2005.

IR: 5.81, 598μ (imide C=O's); 6.10μ (C=C); 6.25, 6.35 (Ar).

NMR (CDCl$_3$): multiplets from 65-160 cps (CH$_2$'s) and singlet at 137 cps (ArCH$_3$) (11H); quartet at 150, 165, 195, 210 cps (CH$_2$CO, 2H); overlapping singlet at 225 cps (OCH$_3$) and triplet at 225, 231, 239 cps (NCH$_2$) (5H); multiplets at 400-435 cps (ArH, 8H); triplet at 442, 446, 449 (=CH, 1H).

B.

N-(p-methylphenethyl)-4a-(m-methoxyphenyl)-1,3-diketo-trans-decahydroisoquinoline

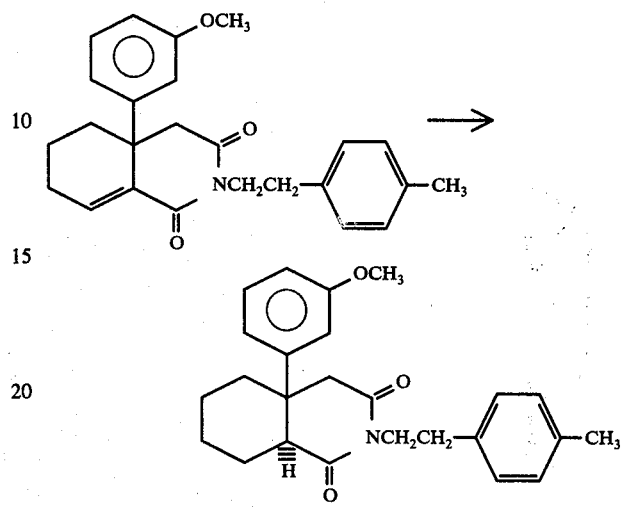

The product from Part A (4.4 g) was reacted with 100 ml of absolute ethanol, 2 g of 5% palladium on carbon and 40 psi of hydrogen. The catalyst was removed by filtration and the solvent evaporated to give crude N-(p-methylphenethyl)-imide, 4.4 g, mp 120°-124°; recrystallized from ethanol, m.p. 132°-133° C.

Anal: Calcd. for $C_{25}H_{29}NO_3$: C, 76.70; H, 7.47; N, 3.58

Found C, 76.65; H, 7.22; N, 3.59.

IR: 5.80, 5.97μ (imide C=O's); 6.25, 6.35μ (Ar).

NMR (CDCl$_3$): multiplets from 50-160 cps (CH$_2$'s) and singlet at 138 cps (ArCh$_3$); quartet at 148, 165, 177, 192 cps (—CH$_2$—CO); overlapping singlet at 224 cps (OCH$_3$) and triplet at 224, 232, 240 cps (NCH$_2$) (5H); multiplets at 395-440 cps (ArH, 8H).

C.

N-(p-methylphenethyl)-4a-(m-methoxyphenyl)-trans-decahydroisoquinoline

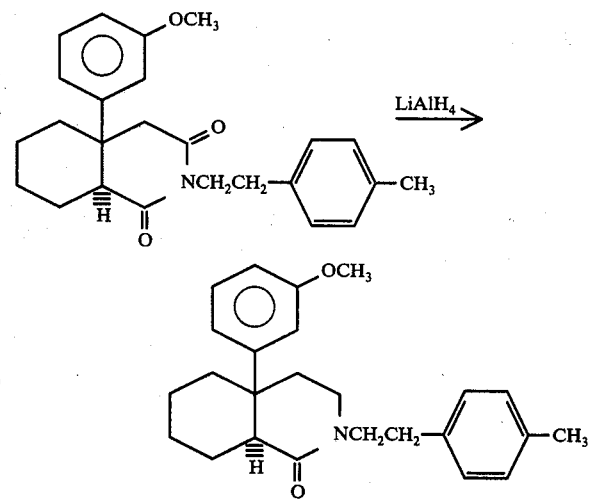

The product from Part B (4.4 g) was reacted under nitrogen with 100 ml of anhydrous tetrahydrofuran and 4.5 g of lithium aluminum hydride at reflux for 18 hours.

It was allowed to cool and then treated successively with water (50 ml), 15% aqueous sodium hydroxide (50 ml), and water (150 ml). Filtration and evaporation of solvent gave a residue which was treated with 400 ml of 1N hydrochloric acid and extracted with ether. The aqueous acidic solution was made basic by addition of potassium hydroxide pellets and then extracted with ether. Concentration of the ether extracts and evaporative distillation of the residue at 160° (2μ) gave 3.0 g.

NMR (CDCl$_3$): multiplets from 50–180 cps (—CH$_2$'s) and singlet at 137 cps (CH$_3$) (22H); singlet at 227 cps (OCH$_3$, 3H); multiplets at 390–435 cps (Ar-H, 8H).

EXAMPLE 2

N-(p-methylphenethyl)-4a-(m-hydroxyphenyl)-trans-decahydroisoquinoline

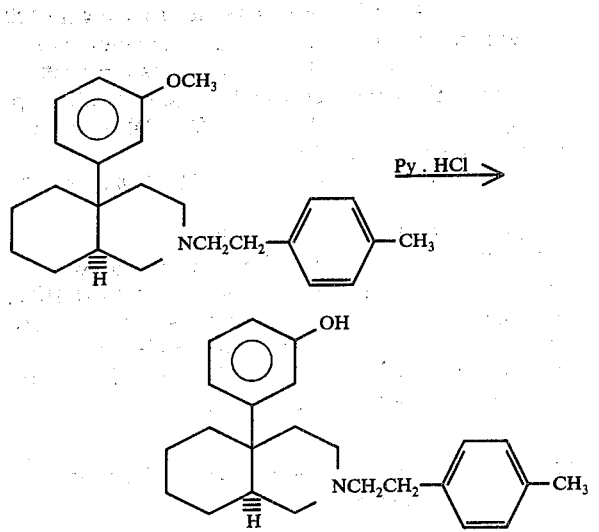

A mixture of the product from Example 1 (2.0 g) and pyridine hydrochloride (8 g) was heated at 200° for 2 hours.

The mixture was cooled, diluted with 150 ml of water and extracted with 150 ml of methylene chloride. The residue from the evaporated organic extracts was mixed with 150 ml of water and solid potassium carbonate until basic and then extracted with methylene chloride.

The residue from evaporation of the methylene chloride was evaporatively distilled to yield 1.5 g, bp 250° (0.1μ). This oil solidified on standing and was recrystallized from ethyl acetate, m.p. 182°–185°.

Anal: Calcd. for C$_{24}$H$_{31}$NO$_3$: C, 82.47; H, 8.94; N, 4.01

Found: C, 82.41; H, 8.84; N, 4.25.

EXAMPLE 3

N-p-methylphenethyl-4a-(m-methoxyphenyl)-6-methyl-trans-decahydroisoquinoline

A.

N-p-methylphenethyl-4a-(m-methoxyphenyl)-6-methyl-1,3-diketo-1,2,3,4,4a,5,6,7-octahydroisoquinoline

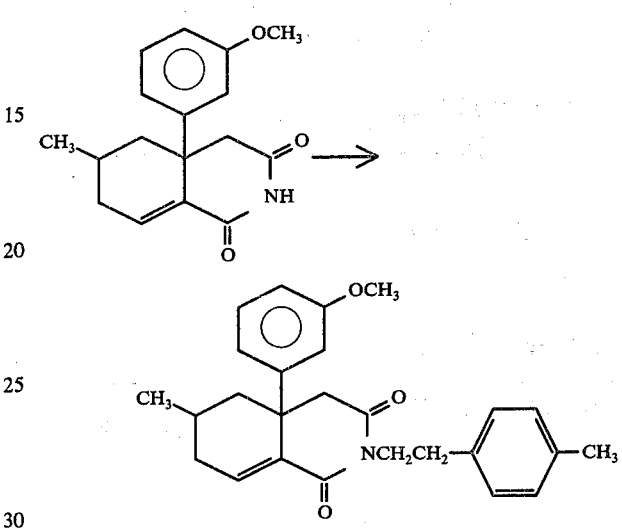

A solution of imide (6.3 g) in 125 ml of anhydrous dimethylformamide was added to 1.2 g of a 55% suspension of sodium hydride in mineral oil and 75 ml of dimethylformamide at 70°. One hour after the addition was complete the reaction was cooled and 5 g of p-methylphenethyl mesylate in 25 ml of dimethylformamide was added. The mixture was warmed to 70° for 2 hours then stirred at 25° for 18 hours. It was poured into water, extracted with ether, and the residue remaining after evaporation of the ether was chromatographed on 300 g of Florisil and eluted with acetone-hexane mixtures to yield 6.25 g.

Anal: Calcd. for C$_{26}$H$_{29}$NO$_3$: C, 77.39; H, 7.24; N, 3.47

Found: C, 77.50; H, 7.42; N, 3.49.

IR: 5.80 and 5.96μ (imide C═O's); 6.05μ (C═C); 6.20 and 6.30μ (Ar).

B.

N-p-methylphenethyl-4a-(m-methoxyphenyl)-6-methyl-1,3-diketo-trans-decahydroisoquinoline

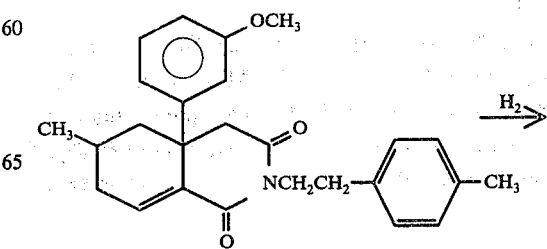

-continued

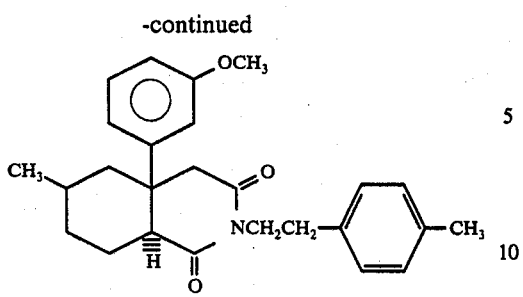

A mixture of 5.5 g of the product from Part A, 150 ml of ethanol, 75 ml of dioxane and 2.5 g of 5% palladium-on-carbon was hydrogenated at 40 psi for 18 hours. The catalyst was filtered off and the filtrate evaporated to yield 5.5 g.

IR: 5.80 and 5.99$\mu$ (imide C=O's); 6.20, 6.30 (Ar).

C.

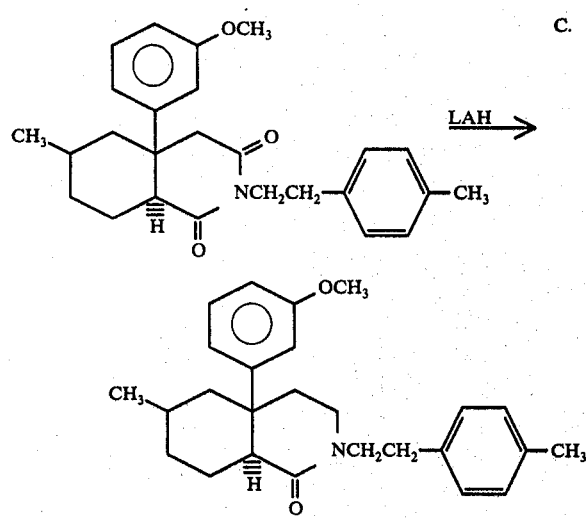

A mixture of 4.75 g of the product from Part B, 150 ml of anhydrous tetrahydrofuran and 5.0 g of lithium aluminum hydride was refluxed for 24 hr. The reaction was quenched by the successive addition of 5 ml of water, 5 ml of 15% sodium hydroxide and 15 ml of water. The inorganic salts were filtered and the filtrate evaporated. Evaporative distillation of the residue yielded 3.7 g, bp 200° (3$\mu$).

EXAMPLE 4

N-p-methylphenethyl-(m-hydroxyphenyl)-6-methyl-trans-decahydroisoquinoline

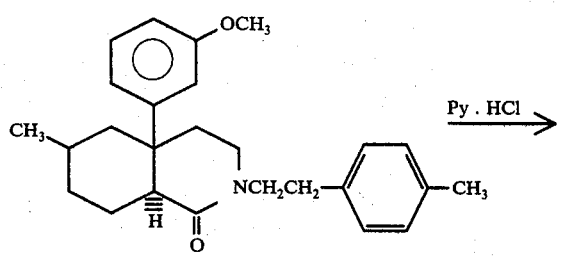

-continued

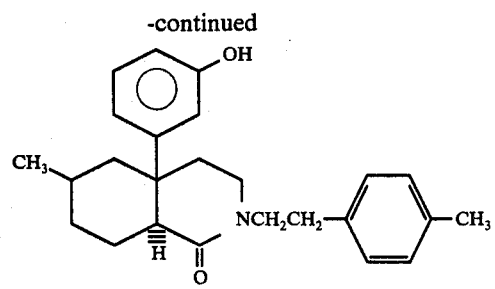

The product form Example 3 (3 g) and 15 g of pyridinehydrochloride were heated at 190° for 1 hour. The mixture was cooled, diluted with water, basified with potassium carbonate and extracted withe methylene chloride. Evaporation of the organic extracts gave a residue which was evaporatively distilled to yield 2.2 g, bp 250° (1$\mu$) and recrystallized from ethyl acetate, m.p. 166°-169°.

Dosage Forms and Use

The analgesic agents of this invention can be administered to alleviate pain by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.01 to 100 milligrams per kilogram of body weight. Ordinarily 0.1 to 50, and preferably 1 to 25 milligrams per kilogram per day given in divided doses 2 to 4 times a day or in sustained release form is effective to obtain desired results.

Dosage forms (compositions) suitable for internal administration contain from about 25 milligrams to about 75 milligrams of active ingredient per unit. In these pharmaceutical compositions the active ingredient will ordinarily be present in an amount of about 0.5 – 95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms; or rectally in the form of suppositories.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suppositories contain the active ingredient in a suitable oleaginous or water-soluble base. The oleaginous class includes cocoa butter and fats with similar properties; the water-soluble class includes polyethylene glycols.

Suitable pharmaceutical carriers are described in Remington's Pharmaceutical Sciences, E. W. Martin, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 50 milligrams of powered active ingredient, 110 milligrams of lactose, 32 milligrams of talc, and 8 milligrams magnesium stearate.

Capsules

A mixture of active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 7 milligrams of ethyl cellulose, 0.2 milligrams of colloidal silicon dioxide, 7 milligrams of magnesium stearate, 11 milligrams of microcrystalline cellulose, 11 milligrams of cornstarch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by filtration.

Suspension

An aqueous suspension is prepared for oral administration so that each 5 milliliters contain 10 milligrams of finely divided active ingredient, 500 milligrams of acacia, 5 milligrams of sodium benzoate, 1.0 gram of sorbitol solution, U.S.P., 5 milligrams of sodium saccharin, and 0.025 milliliters of vanilla tincture.

Injectable

A parenteral composition suitable for administration by injection is prepared by dissolving 1% by weight of active ingredient in sodium chloride injection U.S.P. XV and adjusting the pH of the solution to between 6 and 7. The solution is sterilized by filtration.

Use

A standard procedure for detecting and comparing the analgesic activity of compounds in this series for which there is good correlation with human efficacy is the standard phenylquinone writhing test modified from Siegmund, et. at., *Proc. Soc. Exp. Biol. Med.* 95, 729 (1957). A test compound suspended in 1% methylcellulose was given orally to fasted (17–21 hours) female white mice, 5–20 animals per double blind test. Aqueous (0.01% phenyl-p-benzoquinone) phenylquinone was injected intraperitoneally at 24 minutes later using 0.20 ml per mouse. Commencing at 30 minutes after the oral administration of the test compound, the mice were observed for 10 minutes for a characteristic stretching or writhing syndrome which is indicative of pain induced by phenylquinone. The effective analgesic dose for 50% of the mice (ED 50) was calculated by the moving average method of Thompson, W. R., Bact. Rev. 11, 115–145 (1947).

Narcotic analgesics produce in mice an erection and arching of the tail (90° or more) which is referable to spinal cord stimulation. This straub tail reaction is not produced by other analgesics, including the narcotic antagonists.

The method used was modified from Shemano, I., and Wendel, H., Tox. Appl. Pharm. 6, 334–9 (1964). $CF_1S$ female mice (18–21 g), 10–20 mice per dose were injected intraperitoneally with log scaled doses of analgesic in 1% aqueous methylcellulose. A positive Straub tail response was recorded if a tail was erected 90° or more for 5 seconds at any time within 25 minutes after dosing. A quantal Straub tail $ED_{50}$ was calculated by the moving average method. (Thompson, W. R., Bact. Rev. 11, 115–145 (1947).

The following table shows the Straub tail $ED_{50}$ and analgesic $ED_{50}$ for the compounds of this invention.

TRANS-DECAHYDROISOQUINOLINE ANALGESICS

| Compound | $ED_{50}^{ST}/ED_{50}^{analgesia}$ |
|---|---|
| N-(p-methylphenethyl)-4a-(m-methoxyphenyl)-trans-decahydroisoquinoline | 93/5.8 |
| N-(p-methylphenethyl)-4a-(m-hydroxyphenyl)-trans-decahydroisoquinoline | 93/2 |
| N-(p-methylphenethyl)-4a-(m-methoxyphenyl)-6-methyl-trans-decahydroisoquinoline | >135/8.7 |
| N-(p-methylphenethyl)-4a-(m-hydroxyphenyl)-6-methyl-trans-decahydroisoquinoline | 135/2 |

I claim:

1. A compound of the formula:

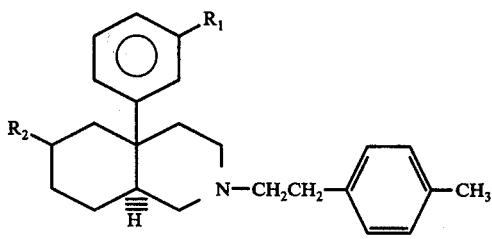

where

R₁ = OH or OCH₃; and

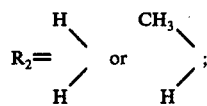

and its pharmaceutically suitable salts.

2. The compound of claim 1: N-(p-methylphenethyl)-4a-(m-methoxyphenyl)-trans-decahydroisoquinoline.

3. The compound of claim 1: N-(p-methylphenethyl)-4a-(m-methoxyphenyl)-trans-decahydroisoquinoline.

4. The compound of claim 1: N-(p-methylphenethyl)-4a-(m-methoxyphenyl)-6-methyl-trans-decahydroisoquinoline.

5. The compound of claim 1: N-(p-methylphenethyl)-4a-(m-hydroxyphenyl)-6-methyl-trans-decahydroisoquinoline.

* * * * *